US009173909B2

(12) United States Patent
Lee

(10) Patent No.: US 9,173,909 B2
(45) Date of Patent: Nov. 3, 2015

(54) IMAGE GUIDED PROTOCOL FOR CELL GENERATION

(71) Applicant: DRVision Technologies LLC, Bellevue, WA (US)

(72) Inventor: Shih-Jong James Lee, Bellevue, WA (US)

(73) Assignee: DRVision Technologies LLC, Bellevue, WA (US)

( * ) Notice: Subject to any disclaimer, the term of this patent is extended or adjusted under 35 U.S.C. 154(b) by 258 days.

(21) Appl. No.: 13/901,553

(22) Filed: May 23, 2013

(65) Prior Publication Data

US 2014/0348409 A1 Nov. 27, 2014

(51) Int. Cl.
*G06K 9/00* (2006.01)
*A61K 35/545* (2015.01)

(52) U.S. Cl.
CPC .......... *A61K 35/545* (2013.01); *G06K 9/00127* (2013.01)

(58) Field of Classification Search
None
See application file for complete search history.

(56) References Cited

U.S. PATENT DOCUMENTS

| | | | |
|---|---|---|---|
| 6,316,215 B1* | 11/2001 | Adair et al. | 435/29 |
| 2003/0179916 A1* | 9/2003 | Magnuson et al. | 382/128 |
| 2005/0260743 A1* | 11/2005 | Drake | C12M 23/44 435/289.1 |
| 2007/0031819 A1* | 2/2007 | Koschwanez et al. | 435/4 |
| 2007/0109874 A1* | 5/2007 | Padfield et al. | 365/189.04 |

* cited by examiner

*Primary Examiner* — Shervin Nakhjavan

(57) ABSTRACT

Computerized image guided control method uses image quantification to dynamically monitor and control the cell generation process. The method acquires images during the cell generation steps and uses computer image analysis to automatically quantify the results of the cell generation steps. In one embodiment, the quantified results from the image analysis are used to determine the readiness of the cell generation step. In another embodiment, a remedial recovery sub-step for the cell generation step is also guided by the imaging results. In yet another embodiment, when a cell generation step is determined to have failed, the cell generation process is early terminated based on image guided decision.

29 Claims, 8 Drawing Sheets

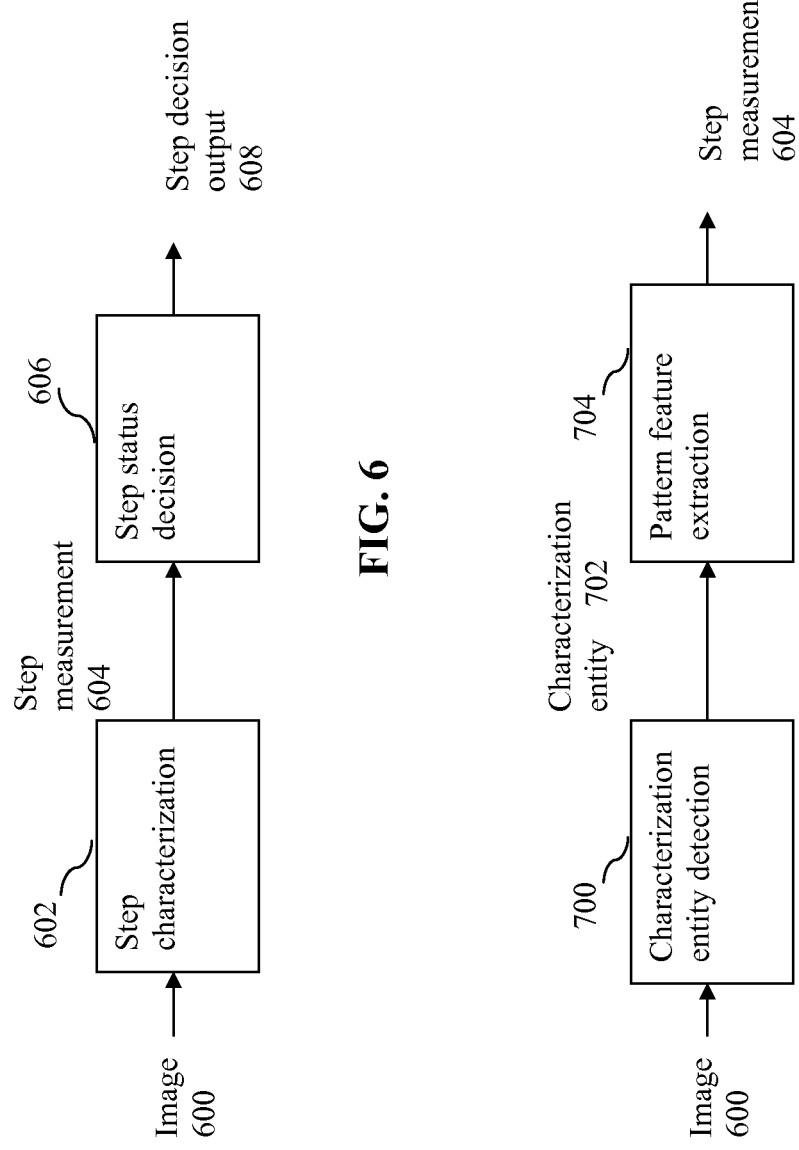

IMAGE GUIDED PROTOCOL FOR CELL GENERATION

STATEMENT AS TO RIGHTS TO INVENTIONS MADE UNDER FEDERALLY SPONSORED RESEARCH AND DEVELOPMENT

This work was supported by U.S. Government grant number 4R44HL106863-02, awarded by the National Heart, Lung, and Blood Institutes. The U.S. Government may have certain rights in the invention.

BACKGROUND OF THE INVENTION

1. Field of the Invention

The present invention relates to image guided protocol for cell generation. More particularly, the present invention relates to computerized image guided methods for determining and controlling readiness, recovery and rejection of steps in cell generation process.

2. Description of the Related Art

The advancement in stem cell technologies enable a new patient-specific or "personalized" medicine paradigm in 1) autologous regenerative medicine; 2) disease cell lines from patient cells for more predictive assays in drug discovery and basic research; and 3) patient-specific cell generation for personalized diagnostic and drug efficacy or adverse effects testing.

The reprogramming (dedifferentiation) of matured cells such as somatic cells to an embryonic-like state, "induced pluripotent stem cells" (iPSCs), offers the prospect of capturing cells derived from a large number of specific types of pre-diagnosed adult patients, potentially at any age, and a correspondingly large number of controls in a format that can support an industrial level of screening, efficacy, and safety studies. However, to achieve the promise of iPSC technology requires the controlled differentiation of iPSCs to specific cell lineages.

An alternative way of producing differentiated cells is by direct reprogramming or called transdifferentiation which is based on prior identification of transcription factors important in lineage specification. For example, it was shown that pancreatic exocrine cells could be converted in vivo to pancreatic β-cells by infecting them with adenovirus expressing three transcription factors, Ngn3, Pdx1 and Mafa, all known to be important for β-cell development. Similarly, direct reprogramming was shown to convert fibroblasts into neurons and cardiac myocytes.

Another possibility is based on partial dedifferentiation with a subsequent differentiation step. Under certain circumstances, this method might allow for sufficient and rapid expansion of a type of progenitor cell still capable of multi-lineage differentiation.

The prior art implementation of the cell generation (differentiation) protocols uses a stepwise differentiation method. It regulates cell generation through sequential stages of differentiation. FIG. 1 shows an ideal stepwise cell generation processing flow. The source cell 100 could be iPSCs, partial dedifferentiation cells, embryonic stem cells or matured cell types such as fibroblasts or bloods. In the generation steps 102, 108, 118 certain factors 104, 110, 116 such as Ngn3, Pdx1 are added and the cell generation process progresses to intermediate states 106, 112, 114. The intermediate states in a β-cell generation protocol could include definitive endoderm, endocrine progenitor, pancreatic progenitor, etc. Note that some direct reprogramming protocols bypass progenitor cell state. But for a general framework, we broadly call the intermediate states as different progenitor cells 106, 112, 114. The generation steps 102, 108, etc. continue until reach the final step (corresponding to generation step K 118 in FIG. 1) and this results in the generation of the target cell 120.

The stepwise approach mimics embryonic development process occurring as a series of generation steps, with cells that have multipotential capacity becoming increasingly differentiated. Protocols producing cardiac myocytes from ESCs and iPSCs by sequentially adding morphogenic factors important in the appearance of cardiac muscle are common now. A typical protocol has predefined generation steps. The duration and the timing and amount for the addition of factors at each generation step are also predefined. However, the yield of the protocols is low. This is partially due to many challenges in the complex environment around the cell generation. Key challenges for a cell generation protocol include efficient induction of the correct germ layer;

correct timing of activation or inhibition of various morphogenic pathways, especially given that the very same pathway can have a stimulatory or an inhibitory influence at different times;

careful control of the concentration of the inducing factors.

Quantitative markers at different stages of development could be used to assess the results of the intermediate stages. As shown in FIG. 2. Marker set 1 200 is used in probe 1 202 to assess progenitor 1 106 for the step 1 confirmation 204. Similarly, Marker set K-1 206 is used in probe K-1 212 to assess progenitor K-1 114 for the step K-1 confirmation 210.

However, the markers themselves exhibit a great deal of variability because there are significant variations among different cell lines, perhaps because individual lines may make variable amounts of their own inducing factors. In addition, markers introduce additional cost and could have adverse side-effect such as toxicity to the cell generation protocol. Therefore, quantification markers are not desirable in practical clinical laboratory settings. Markers are often used only during the protocol development stage to figure out the proper generation step, duration and timing. During the implementation of the protocol, only a limited number of simple markers could be used, especially for the mass production of patient-specific cells. It is desirable to quantify using non-invasive imaging modalities such as phase contrast images without markers that often require florescence imaging. The low yield and the lack of adequate feedback during the protocol implementation represent a significant hurdle of production level cell generation.

BRIEF SUMMARY OF THE INVENTION

To overcome the challenges to achieve high yield cell generation, this invention describes an image guided method that uses image quantification to dynamically control the cell generation process. It consists of an imaging microscope to acquire images during the cell generation steps and uses computer image analysis to automatically quantify the outcomes of the generation steps. In one embodiment of the invention, the quantification results are used to determine the readiness of the generation step and can predict the timing and the concentration of the inducing factors for the next generation step. In another embodiment of the invention, a remedial sub-step for the current generation step could also be guided by the imaging results. In another alternative embodiment of the invention, when a cell generation step is considered to have failed the cell generation process can be early terminated based on image guided decision.

The primary objective of the invention is to provide a high yield cell generation protocol using dynamic control through image guidance. The second objective of this invention is to provide a recovery sub-step to correct the deviated cell generation process. The third objective of this invention is to provide a failure detection method to early terminate the cell generation process that can avoid wasteful processing. The fourth objective of this invention is to provide a dynamic control method that does not require extensive markers to reduce the cell generation cost and labor.

BRIEF DESCRIPTION OF THE DRAWINGS

FIG. 6 shows the processing flow of the image guided decision of the image guided method according to the present application.

FIG. 7 shows the processing flow of the step characterization of the image guided decision according to the present application.

DETAILED DESCRIPTION OF THE INVENTION

The methods according to the present application are described in detail below in conjunction with the accompanying drawings.

I. Application Scenarios

The present invention uses image quantification to dynamically control the cell generation protocol. In different embodiments of the invention, the image guided dynamic controls include a step readiness control, a step recovery control, a step rejection control and combinations of them.

A. Image Guided Step Readiness Control

Figure 1:
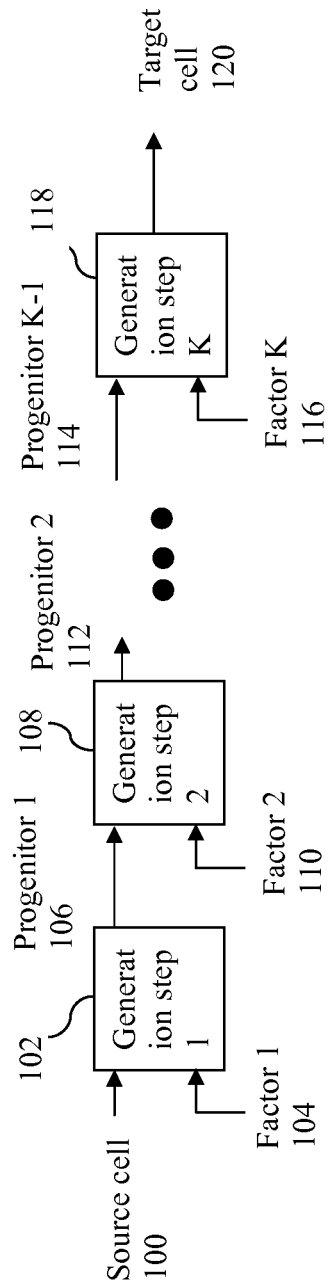
FIG. 1 shows an ideal stepwise cell generation processing flow.
Figure 2:
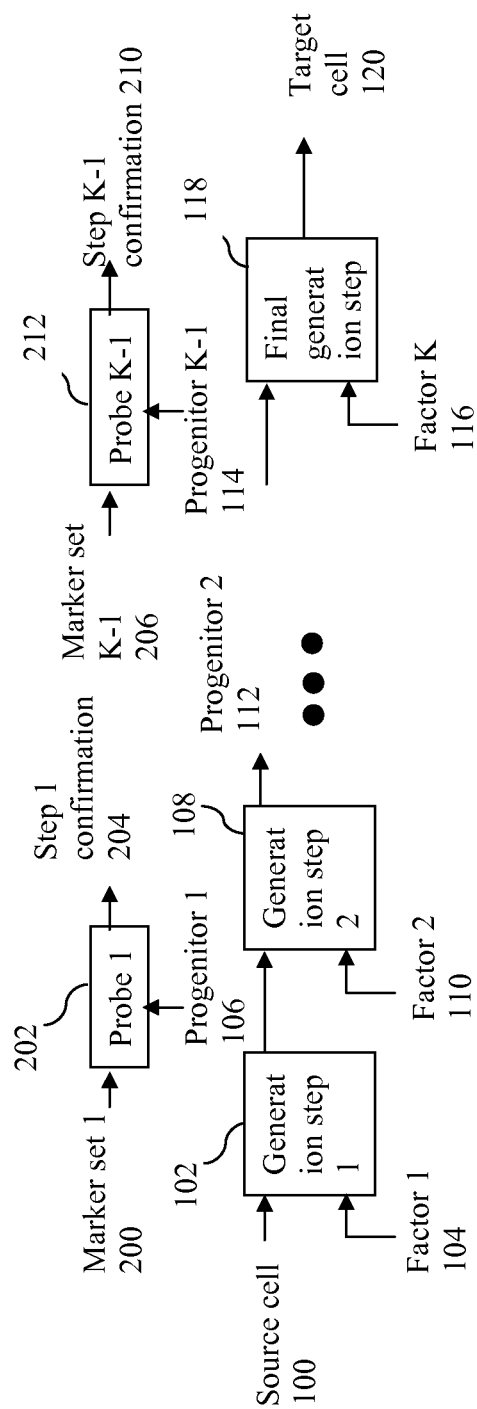
FIG. 2 shows the stepwise cell generation processing flow incorporating quantitative markers.
Figure 3:
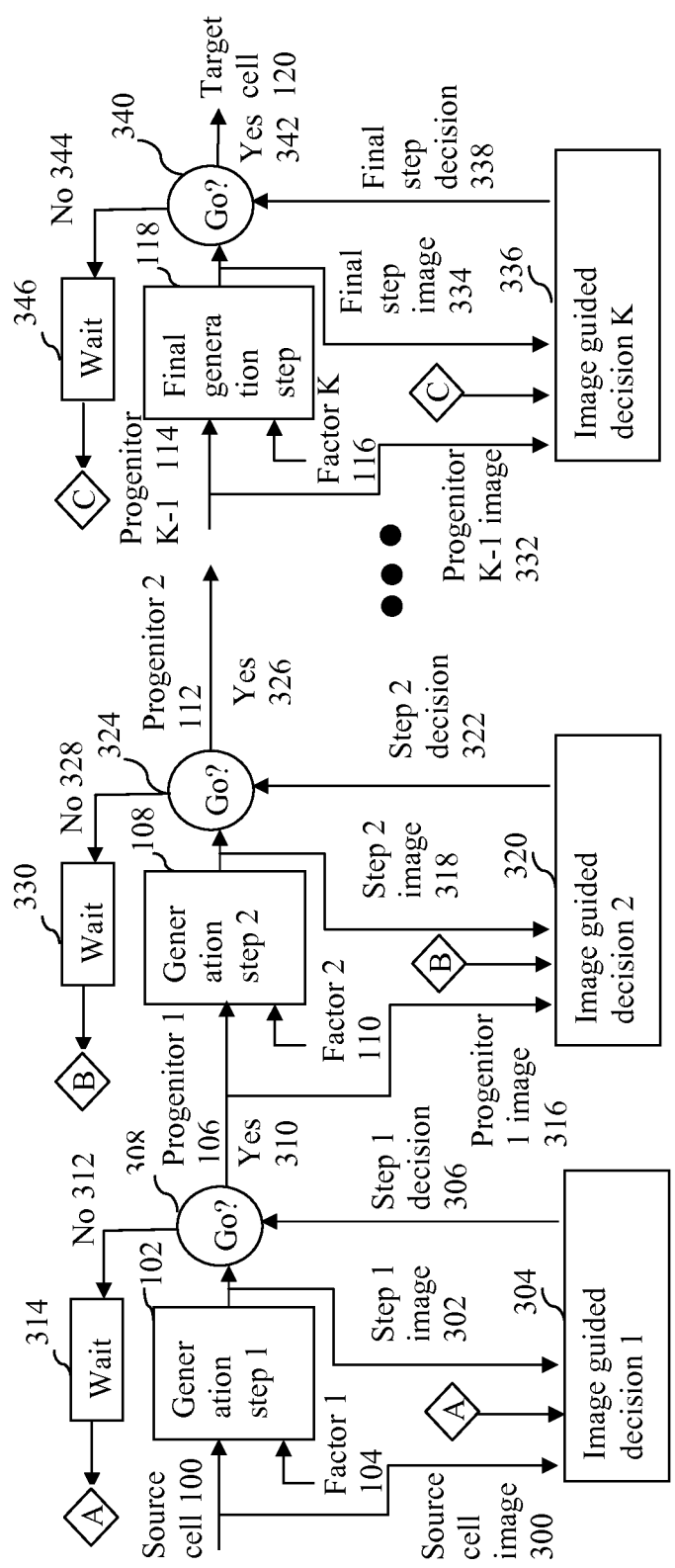
FIG. 3 shows the processing flow of the image guided step readiness control method according to the present application.

FIG. 3 illustrates the computerized image guided step readiness control processing flow. An image guided decision module 304, 320, 336 is included to monitor and control each of the cell generation steps 102, 108, 118. In one embodiment of the invention, the image guided decision 1 module 304 acquires a step 1 image 302 when the generation step 1 102 is ready to be checked for readiness. In another embodiment of the invention, the module also acquires a source cell image 300 at the start of the generation step 1 102. This could be done before and/or after the factor 1 104 is induced. In yet another embodiment of the invention, time-lapse images are acquired at a plurality of time points during generation step 1 102. The image guided decision 1 module 304 processes the acquired images 302, 300 and outputs a step 1 decision 306. If the "Go?" decision 308 outcome is "Yes" 310 (that is, a "Go" decision output), the generation step 1 102 is considered ready and the cell generation process will continue toward generation step 2 108 wherein the factor 2 110 will be induced to the cell culture.

If the "Go?" decision 308 outcome is "No" 312 (that is, a "No-Go" decision output), the generation step 1 102 is considered not ready and the cell generation process will be in a Wait 314 state. That is, generation step 1 102 will be stayed until a waiting period is reached and the image guided decision 1 module 304 will repeat the decision making process. This process continues until a "Yes" 310 status is reached in the "Go?" decision 308 or until a maximum number of allowable decision attempts is reached. In the case that the maximum number of allowable decision attempts is reached, the cell generation process will be terminated. In one embodiment of the invention, the maximum number of allowable decision attempts can be specified by a user of a step. In another embodiment of the invention, the maximum number of allowable decision attempts can be dynamically determined.

For a successful "Go?" decision 308, 324, 340 in one generation step (for example Generation step 1 102), the image guided decision process continues to the next generation step (for example Generation step 2 108) and the output of the current step is the progenitor outcome (for example progenitor 1 106). Then the same readiness control is applied to the next generation step (for example Generation step 2 108). This process 316, 318, 320, 322, 324, 326, 328, 330, . . . , 332, 334, 336, 338, 340, 342, 344, 346 continues until the target cell 120 is successfully generated or the cell generation process is early terminated. Note that depending on the cell generation protocol, the image guided decision may only be applied to a single or just a few key generation steps of the protocol. That is, not all generation steps 102, 108, 118 require the image guided decision steps 304, 320, 336.

B. Image Guided Step Recovery Control

Figure 4:
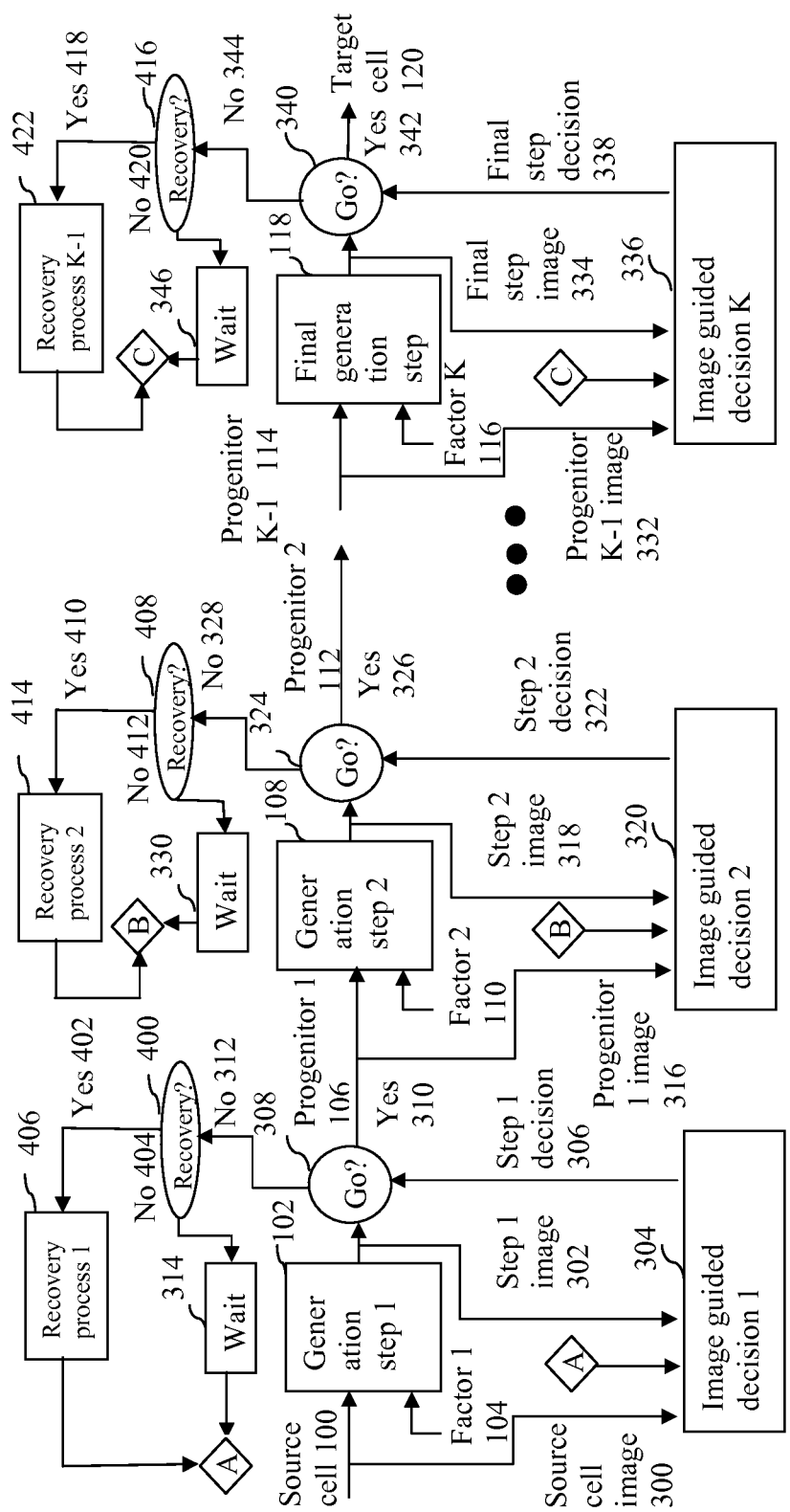
FIG. 4 shows the processing flow of the image guided step recovery control method according to the present application.

FIG. 4 illustrates the image guided step recovery control processing flow. An image guided decision module 304, 320, 336 is included to monitor and control each of the cell generation steps 102, 108, 118. In one embodiment of the invention, the image guided decision 1 module 304 acquires a step 1 image 302 when the generation step 1 is ready to be checked for recovery control 400. In another embodiment of the invention, the module also acquires a source cell image 300 at the start of the generation step 1 102. This could be done before and/or after the factor 1 104 is induced. In yet another embodiment of the invention, time-lapse images are acquired at a plurality of time points during generation step 1 102. The image guided decision 1 module 304 processes the acquired images 302, 300 and outputs a step 1 decision 306. Just like the step readiness control in Section A and FIG. 3, if the "Go?" decision 308 outcome is "Yes" 310 (that is, a "Go" decision output), the generation step 1 102 is considered ready and the cell generation process will continue toward generation step 2 108 wherein the factor 2 110 will be induced to the cell culture.

If the "Go?" decision 308 outcome is "No" 312, the generation step 1 102 is not ready and a "Recovery?" check 400 is performed. The "Recovery?" check 400 determines whether the generation step 1 102 could become ready by just waiting in a wait state 314 or a recovery process 1 406 has to be performed to generation step 1 102 cell culture to correct the deviation from expected generation step 1 102 outcome. If the "Recovery?" check 400 outcome is "Yes" 402 (that is, a "No-Go Recovery" decision output), a recovery process 1 406 is applied to generation step 1 102 and the image guided decision 1 module 304 will repeat making the step 1 decision 306 after the recovery process 1 406 is fully performed. In one embodiment of the invention, the recovery process 1 406 induces additional factor 1 104 to the generation step 1 102. In another embodiment of the invention, the recovery process 1 406 induces other factors to promote desired outcomes and/or suppress undesired outcomes.

If the outcome of the "Recovery?" check 400 is "No" 404 (that is, a "No-Go Wait" decision output), the cell generation process will stay in a Wait state 314 of the generation step 1 102 until a waiting period is reached and the image guided decision 1 module 304 will repeat making the step 1 decision 306. This process continues until a "Yes" 310 status is reached in the "Go?" decision 308 or until a maximum number of allowable decision attempts is reached. In the case that the maximum number of allowable decision attempts is reached, the cell generation process will be terminated. In one embodiment of the invention, the maximum number of allowable decision attempts can be specified by a user of a step. In another embodiment of the invention, the maximum number of allowable decision attempts can be dynamically determined.

For a successful "Go?" decision 308, 324, 340 in one generation step (for example Generation step 1 102), the image guided decision process continues to the next generation step (for example Generation step 2 108) and the output of the current step is the progenitor outcome (for example progenitor 1 106). Then the same recovery control is applied to the next generation step (for example Generation step 2 108). This process 316, 318, 320, 322 324, 326, 328, 408, 410, 412, 414, 330, . . . , 332, 334, 336, 338, 340, 342, 344, 346, 416, 418, 420, 422 continues until the target cell 120 is successfully generated or the cell generation process is early terminated. Note that depending on the cell generation protocol, the image guided decision may only be applied to a single or just a few key generation steps of the protocol. That is, not all generation steps 102, 108, 118 require the image guided decision 304, 320, 336.

C. Image Guided Step Rejection Control

Figure 5:
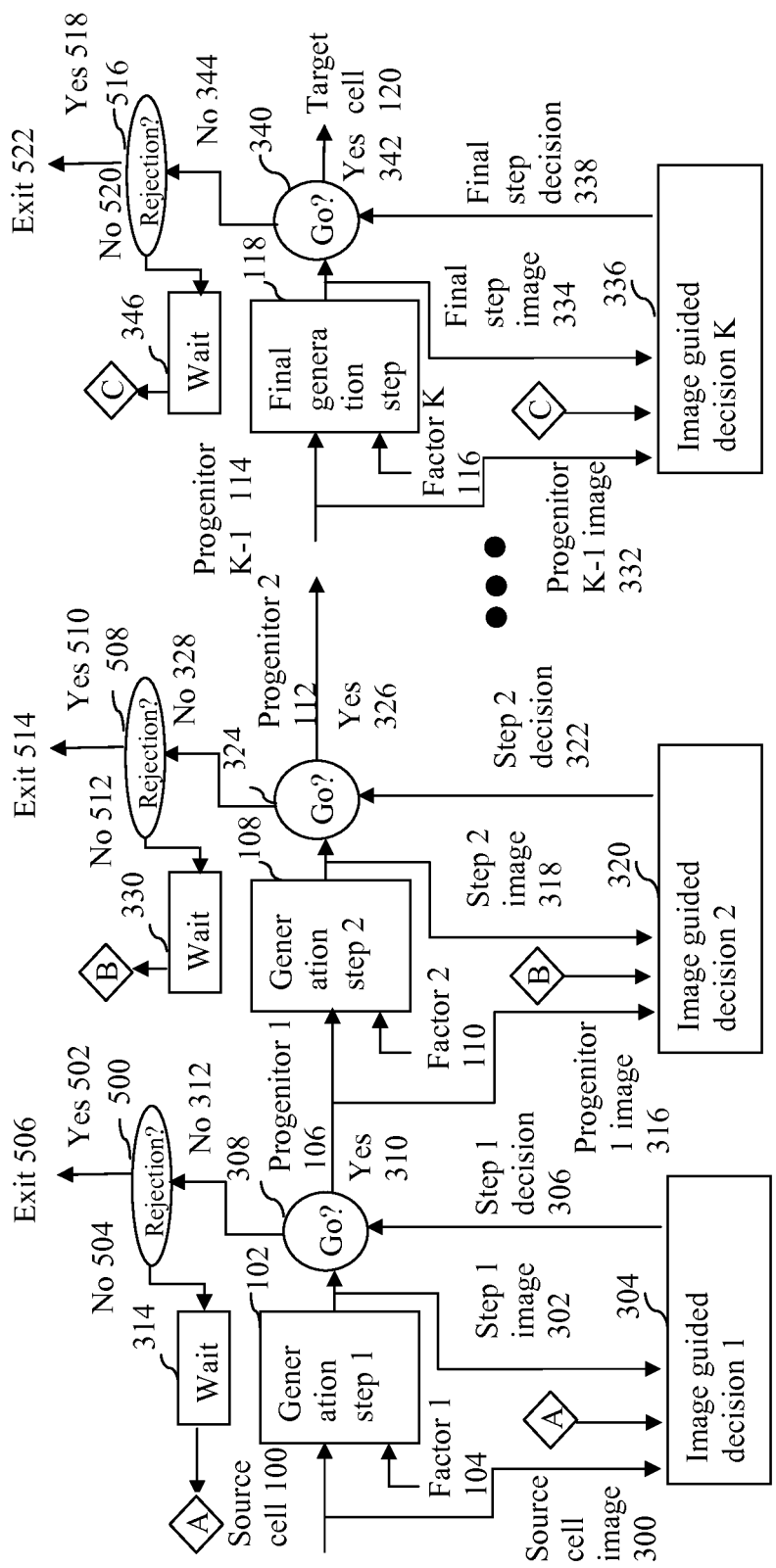
FIG. 5 shows the processing flow of the image guided step rejection control method according to the present application.

FIG. 5 illustrates the image guided step rejection control processing flow. An image guided decision module 304, 320, 336 is included to monitor and control each of the cell generation steps 102, 108, 118. In one embodiment of the invention, the image guided decision 1 module 304 acquires a generation step 1 image 302 when the generation step 1 102 is ready to be checked for rejection control. In another embodiment of the invention, the module also acquires a source cell image 300 at the start of the generation step 1 102. This could be done before and/or after the factor 1 104 is induced. In yet another embodiment of the invention, time-lapse images are acquired at a plurality of time points during generation step 1 102. The image guided decision 1 module 304 processes the acquired images 300, 302 and outputs a step 1 decision 306. Just like the image guided controls in Section A (for step readiness) and Section B (for step recovery), if the "Go?" decision 308 outcome is "Yes" 310 (that is, a "Go" decision output), the generation step 1 102 is considered ready and the cell generation process will continue toward generation step 2 108 wherein the factor 2 110 will be induced to the cell culture.

If the "Go?" decision 308 outcome is "No" 312, the generation step 1 102 is not ready and a "Rejection?" check 500 is performed. The "Rejection?" check 500 determines whether the generation step 1 102 has deviated so much from the expected generation step 1 102 outcome that the cell generation process should be terminated to avoid wasteful processing. If the "Rejection?" check 500 outcome is "Yes" 502 (that is, a "No-Go Rejection" decision output), the cell generation process is terminated at the exit 506. If the "Rejection?" check 500 outcome is "No" 504 (that is, a "No-Go Wait" decision output), the cell generation process will stay in the wait state 314 of generation step 1 102 until a waiting period is reached and the image guided decision 1 module 304 will repeat making the step 1 decision 306. This process continues until a "Yes" 310 status is reached in the "Go?" decision 308 or the cell generation process will be terminated if a "Yes" 502 status is reached in the "Rejection?" check 500 or a maximum number of allowable decision attempts is reached. In one embodiment of the invention, the maximum number of allowable decision attempts can be specified by a user of a step. In another embodiment of the invention, the maximum number of allowable decision attempts can be dynamically determined.

For a successful "Go?" decision 308, 324, 340 in one generation step (for example Generation step 1 102), the image guided decision process continues to the next generation step (for example Generation step 2 108) and the output of the current step is the progenitor outcome (for example progenitor 1 106). Then the same recovery control is applies to the next generation step (for example Generation step 2 108). This process 316, 318, 320, 322, 324, 326, 328, 508, 510, 512, 330, . . . , 332, 334, 336, 338, 340, 342, 344, 346, 516, 518, 520 continues until the target cell 120 is successfully generated or the cell generation process is early terminated. Note that depending on the cell generation protocol, the image guided decision may only be applied to a single or just a few key generation steps of the protocol. That is, not all generation steps 102, 108, 118 require the image guided decision 304, 320, 336.

II. Image Guided Decision

As shown in FIG. 6, the image guided decision module inputs at least one image 600, it performs step characterization 602 to generate at least one step measurement 604 and makes a step status decision 606 based on the at least one step measurement 604 and outputs a step decision output 608.

II.1 Image

The input image 600 could include one or more florescence image labeled with markers to detect progenitors of different generation steps. It could include a 3D image acquired from 3D microscopes such as confocal, super-resolution, or multiple Z images via deconvolution. The image could include label free image acquired from phase contrast, differential interference contrast (DIC) and/or bright field microscopes. It could include a combination of different imaging modalities. The input image could also include a single image, a plurality of images or a time-lapse image sequence.

II.2 Step Characterization

The step characterization module 602 inputs image 600 and performs characterization entity detection 700 and outputs characterization entity 702. It then performs pattern feature extraction 704 from the characterization entity 702 and outputs step measurements 604, as shown in FIG. 7.

A. Characterization Entity Detection

A characterization entity 702 is the basic unit for direct measurements. Depending on the cell generation protocol, the characterization entity 702 could include individual cell, a cell colony, a grid region of the image or the whole image in 2D or 3D.

A.1 Cell or Colony Detection

Cell or colony detection can be performed by an image segmentation process. In one embodiment of the invention, a structure guided processing method as described in Lee; Shih-Jong J. "Structure-guided image processing and image feature enhancement", U.S. Pat. No. 6,463,175, Sep. 24, 2002 and Lee; Shih-Jong J., Oh; Seho, Huang; Chi-Chou, "Structure-guided automatic learning for image feature enhancement" U.S. Pat. No. 6,507,675, Jan. 14, 2003 can be used for image segmentation.

In another embodiment of the invention, the teachable segmentation method as described in Lee; Shih-Jong J., Oh; Seho "Learnable Object Segmentation", U.S. Pat. No. 7,203,360, Apr. 10, 2007 can be used for image segmentation.

In alternative embodiments of the invention, segmentation methods such as thresholding, watershed, modeling, clustering methods can also be used for the characterization entity detection.

For time-lapse image sequence, the detected cells and/or colonies can be tracked and the trajectory over time can be used as the characterization entity. In this case, pattern dynamics such as the changes of size, shape, intensities, textures over time can be characterized for each characterization entity. The cell tracking method described in Lee; Shih-Jong J., Oh; Seho "Method for moving cell detection from temporal image sequence model estimation", U.S. Pat. No. 8,045,783, Oct. 25, 2011 can be used for tracking. In alternative embodiments of the invention, other tracking methods such as autocorrelation, Kalman filter, etc. can also be used for tracking A.2 Grid Region Determination In some steps of the cell generation protocol, it is difficult to identify individual cells or colonies. In this case, grid region can be used as the characterization entity. Simple grids are regularly spaced regions in an image. More sophisticated grids can be created by stratified or random sampling of regions in an image. The number and size of the grid regions can be determined by image and expected pattern sizes. In alternative embodiments of the invention, other grid determination methods such as checkerboard patterning can also be used for the characterization entity determination.

For time-lapse image sequence, the grids can be tracked by simply associating the same region overtime as the characterization entity.

A.3 Whole Image

In some steps of the cell generation protocol, it is difficult to identify individual cells or colonies and it is meaningless to divide image into grids. In this case, the whole image can be used as the characterization entity.

Furthermore, the whole image summary characterization for all characterization entities such as cells, colonies or grids from the same image can be generated. The summary characterization could include mean, median, percentiles and standard deviation, skewness and kurtosis of the characterization entities common to an image.

B. Pattern Feature Extraction

To facilitate the step status decision 606, pattern features are extracted from the characterization entities. A comprehensive set of pattern features can be extracted from a single or a plurality of characterization entities. In one embodiment of the invention, the representative features include intensity space features, color space features and relational features. For time-lapse images, kinetic features can also be extracted.

B.1 Intensity Space Features

The features are derived from the grayscale intensity in the region of a characterization entity such as mean, standard deviation, skewness, kurtosis and other statistics. Moreover, pre-processing of the grayscale intensity can be performed before extracting the statistics. The pre-processing includes point operations such as logarithm conversion for optical density measurement or filtering such as edge enhancement by linear or morphological gradient operator that includes dark edge, bright edge, general edge enhancement, line enhancement, corner enhancement, etc.

Note that when there are multiple channel images derived from different markers and/or imaging modalities, the intensity space features from each of the different channels can all be included.

In alternative embodiments of the invention, other intensity space features such as texture features derived from co-occurrence matrices or wavelet, run-lengths etc. could be used.

B.2 Color Space Features

When the input image is a color image, color transformation may be applied to convert the color image into multi-bands of grayscale images. In one embodiment of the invention, the multiple bands includes the following images: R (Red channel), G (Green channel), B (Blue channel), (R-G)/(R+G), R/(R+G+B), G/(R+G+B), B/(R+G+B), R/G, R/B, G/B, G/R, B/G, B/R, etc. In addition, RGB to HSI conversion can be performed to generate hue, saturation, and intensity bands.

The intensity space features with and without pre-processing as described in section B.1 can be generated for each band of the image.

In alternative embodiments of the invention, other feature spaces such as temporal space or different focal planes could be used.

B.3 Relational Features

Relational features can characterize spatial relations of multiple sets of objects by comprehensive collections of spatial mapping features. Some of the features have clearly understandable physical, structural, or geometrical meanings Others are statistical characterizations, which may not have clear physical, structural or geometrical meanings when considered individually. A combination of these features could characterize subtle difference numerically using the comprehensive feature set.

In one embodiment of the invention, the relational feature extraction method as described in Lee; Shih-Jong J., Oh; Seho "Intelligent Spatial Reasoning", U.S. Pat. No. 7,263,509, Aug. 28, 2007 can be used for relational features.

B.4 Kinetic Features

When the characterization entities include trajectories from time-lapse image sequence, the pattern features can include kinetic features such as the changes in intensity space, color space and relational features as well as the change velocity, change acceleration of the trajectories and their pattern features.

B.5 Summary Features

The whole image summary features for all characterization entities such as cells, colonies or grids from the image can be generated. The summary features include summary statistics such as mean, variance, skewness, kurtosis, median, and top and bottom percentiles of the pattern features from the characterization entities of the image.

The characterization entity features and/or their summary features are included in the at least one step measurement 604. Step measurements form a feature vector that can be used by the step status decision module 606 to generate a step decision output 608.

II.3 Step Status Decision

Figure 8:
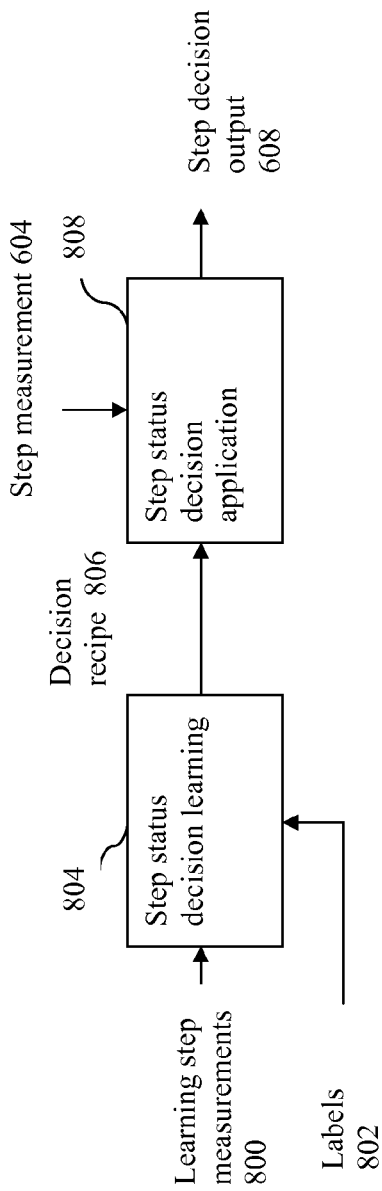
FIG. 8 shows the processing phases of the step status decision of the image guided decision according to the present application.

Step status decision includes a step status decision learning 804 phase and a step status decision application 808 phase as shown in FIG. 8. Learning step measurements 800 are inputted to the step status decision learning 804 step to generate a decision recipe 806 and the decision recipe 806 is used to process the at least one step measurement 604 in the step status decision application 808 phase to generate step decision output 608.

In the step status decision learning 804 phase, the learning step measurements 800 of each generation step can be associated with a desired generation step status outcome. The desired generation step status outcomes can be derived from the cell generation actual outcomes from learning phase and with a comprehensive generation step marker set. The desired generation step status outcomes are the labels 802 for the step measurement feature vectors that can be used for step status decision learning 804.

In one embodiment of the invention, the decision labels are "Go", "No-Go" or "Yes" and "No" for a "Go?" decision step in the image guided step readiness control. In another embodiment of the invention, the decision labels are "Go", "No-Go Recovery", "No-Go Wait" or "Yes" and "No" for a "Go?" decision step and "Yes" and "No" for a "Recovery?" decision step in the image guided step recovery control. In yet another embodiment of the invention, the decision labels are "Go", "No-Go Rejection", "No-Go Wait" or "Yes" and "No" for a "Go?" decision step and "Yes" and "No" for a "Rejection?" decision step in the image guided step rejection control.

The step status decision learning 804 generates decision recipe 806 that can be used in the step status decision application 808 phase using the at least one step measurement 604 generated from the cell generation steps for step status decision application 808. The step status decision application 808 generates a step decision output 608 that is used to control the cell generation process.

A. Step Status Decision Learning

Figure 9:
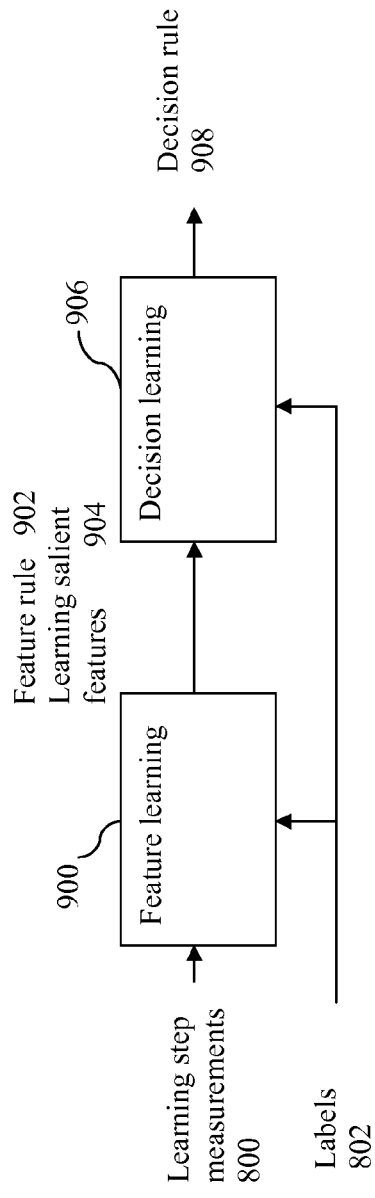
FIG. 9 shows the processing flow of the step status decision learning phase of the step status decision according to the present application.

The step status decision learning 804 includes a feature learning 900 and a decision learning 906 stage. As shown in FIG. 9, the learning step measurements 800 and labels 802 are used for feature learning 900 to generate feature rule 902 and the learning salient features 904 generated from applying the feature rule 902 to the learning step measurements 800. The learning salient features 904 and the labels 802 are used by the decision learning 906 stage to generate a decision rule 908 output. The feature rule 902 and decision rule 908 are collectively the decision recipe 806.

In alternative embodiments of the invention, the feature learning could be effectively bypassed in simple cell generation protocols. In this case, the feature rule could be no operation and the learning salient features could be the same as the learning step measurements.

A.1 Feature Learning

In one embodiment of the invention, feature learning can include feature selection and feature transformation modules. They can be applied separately or in combination.

A.1.1 Feature Selection

Feature selection method selects a subset of features that could discriminate between different labels. Feature selection reduces the dimensionality of the step measurements to be processed by the decision stage, reducing execution time and improving decision accuracy.

In one embodiment of the invention, the feature selection method described in Lee; Shih-Jong J., Oh; Seho, Kim; Donglok, "Feature Regulation for Hierarchical Decision Learning", U.S. Pat. No. 7,233,931, Jun. 19, 2007 can be used for feature selection.

In another embodiment of the invention, the CFS (Correlation-based Feature Selection) can be used for feature selection. The CFS algorithm is based on the following hypothesis: a good feature subset is one that contains features highly correlated with (predictive of) the label class, yet uncorrelated with (not predictive of) each other. Other feature selection method such as Branch and bound method, sequential forward selection method, sequential backward selection method could also be used.

In alternative embodiments of the invention, other feature commonly used pattern recognition feature selection methods could be used.

A.1.2 Feature Transformation

Feature transformation method transforms the original feature set into a smaller set of derived features. The decision classifier can then run on this derived set of features. Examples are principal components analysis, factor analysis and independent components analysis. Such techniques can result in reasonable decision performance.

In one embodiment of the invention, the principal components analysis method is used for feature transformation. It is a dimensionality reduction technique, in which d-dimensional data vectors are mapped onto vectors in a new M-dimensional space, where M<d. To do this, the mean and covariance matrices of the data are calculated, and the best M dimensional linear representation of the data is formed by the mean plus the projection of the data onto the eigenvectors of the covariance matrix corresponding to the M largest eigenvalues.

In alternative embodiments of the invention, other commonly used pattern recognition feature transformation methods could be used.

The resulting feature selection and/or feature transformation rules are the feature rule 902 for the decision recipe 806. The feature rule is applied to the learning step measurements to generate learning salient features output.

A.2. Decision Learning

After feature learning, learning salient features 904 are generated. The learning salient features 904 are used to perform decision learning 906. The decision learning is achieved by the supervised learning method. It creates a decision classifier that assigns a salient feature vector into one of the decision output specified by the labels 802.

A number of different supervised learning methods can be used such as decision tree, support vector machine, neural networks, K-nearest neighbor classifier, kernel-based classifier (such as Parzen windows), finite mixture models, Fisher's linear, Bayes quadratic, etc.

In one embodiment of the invention, decision tree classifier is used for decision learning (see Lee; Shih-Jong J. "Regulation of hierarchic decisions in intelligent systems", U.S. Pat. No. 7,031,948, Apr. 18, 2006; Lee; Shih-Jong J. "Information Integration Method for Decision Regulation in Hierarchic Decision Systems", U.S. Pat. No. 7,293,000, Nov. 6, 2007). Decision trees represent a learned function for classification of discrete-valued target functions. Decision trees classify novel items by traversing the tree from the root down to a leaf node, which assigns a classification to the item.

In challenging classification situation, boosting and bagging scheme can be used to enhance the results of the decision tree classifier. However, this will result in more computationally expensive decision classifiers.

Boosting is applied to improve the decision algorithm's accuracy. Boosting works by repeatedly invoking a weak learner (a learning algorithm for which the training set error rate is only slightly better than that of random guessing) on a set of training samples, over which a distribution is maintained. This distribution starts off as a uniform distribution, but is adapted so that, in each iteration, the weight given to incorrectly classified training examples increases. As such, the weak learner must give greater emphasis to the hard samples in the training set.

Bagging (bootstrap aggregation) is a very simple method of manipulating the training data set. A bootstrap sample is generated by uniformly sampling m instances from the training set with replacement. A classifier is then built from the bootstrap sample. This process is repeated several times, and the final classifier is constructed by taking a majority vote of the classifiers built using the bootstrap replicates.

The supervised learning result is the decision rule 908 to be included in the decision recipe 806.

In alternative embodiments of the invention, other pattern recognition and classification methods could be used.

B. Step Status Decision Application

After step status decision learning 804, the decision recipe 806 is stored. New images can then be processed by the step characterization 602 module to generate at least one step measurement 604. The at least one step measurement 604 along with the decision recipe 806 is processed by the step status decision application 808 module to generate the step decision output 608.

Figure 10:
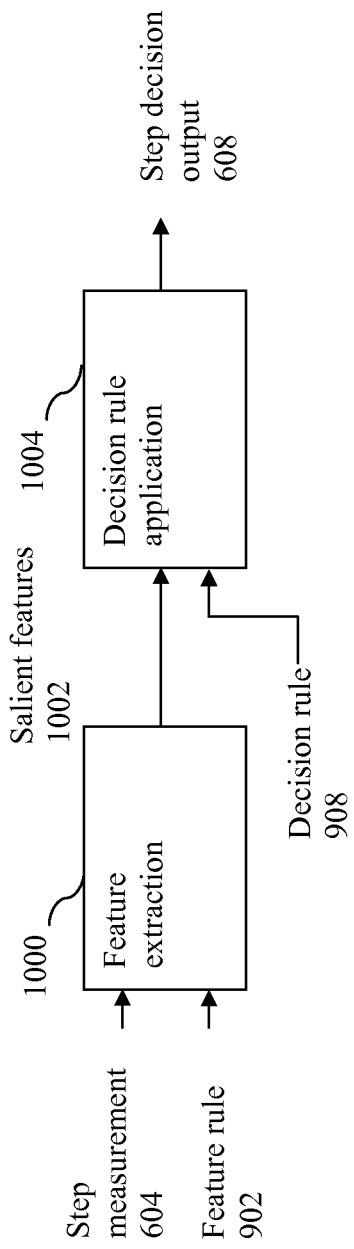
FIG. 10 shows the processing flow of the step status decision application phase of the step status decision according to the present application.

The step status decision application 808 is a relatively straightforward process. It includes a feature extraction 1000 step and a decision rule application 1004 step as shown in FIG. 10. The features to be extracted are specified in the feature rule 902 that is included in the decision recipe 806. The feature extraction 1000 step applies the feature rule 902 for feature selection and/or feature transformation to generate salient features 1002 for the input at least one step measurement 604.

After feature extraction 1000, the decision rule 908 included in the decision recipe 806 can be applied to the extracted salient features 1002 in the decision rule application 1004 module. The decision rule classification results are the step decision output 608 reflecting the labels assigned by the decision rule for the at least one step measurement 604. The decision outcomes include "Go", "No-Go", or "No-Go Recovery", or "No-Go Rejection", or "No-Go Wait" depending on the cell generation protocol and the image guided control methods.

The invention has been described herein in considerable detail in order to comply with the Patent Statutes and to provide those skilled in the art with the information needed to apply the novel principles and to construct and use such specialized components as are required. However, it is to be understood that the inventions can be carried out by specifically different equipment and devices, and that various modifications, both as to the equipment details and operating procedures, can be accomplished without departing from the scope of the invention itself.

What is claimed is:

1. A computerized image guided step readiness control method for cell generation having a plurality of generation steps, said method comprising the steps of:
    a) providing at least one source cell and a factor 1 into a cell culture for a cell generation process;
    b) performing generation step 1 in the cell culture by inducing-the factor 1 to the at least one source cell to obtain a step 1 output;
    c) acquiring a step 1 image into a computer from the step 1 output and performing a computerized image guided decision for the generation step 1 by performing computer image analysis of the step 1 image on the computer to obtain a computerized step 1 decision output;
    d) if the computerized step 1 decision output is "No-Go", waiting for a waiting period; then repeating step c) if a maximum number of allowable decision attempts is not reached, or exiting cell generation if the maximum number of allowable decision attempts is reached; and
    e) if the computerized step 1 decision output is "Go", performing a next generation step in the cell culture by inducing a next factor to the step 1 output to obtain a next step output.

2. The computerized image guided step readiness control method of claim 1, further comprising the steps of:
    f) acquiring a next step image from the next step output and performing a computerized image guided decision for the next generation step by performing computer image analysis of the next step image to obtain a computerized next step decision output;
    g) if the computerized next step decision output is "No-Go", waiting for a waiting period, and then repeating step f) if a maximum number of allowable decision attempts is not reached, or exiting cell generation if the maximum number of allowable decision attempts is reached;
    h) performing an additional generation step by inducing an additional factor to the next step output if the computerized next step decision output is "Go" and the next generation step is not a final generation step; and
    i) completing cell generation to obtain target cell if the next generation step is the final generation step.

3. The computerized image guided step readiness control method of claim 1, wherein the method further acquires a source cell image and the image guided decision uses the step 1 image and the source cell image.

4. The computerized image guided step readiness control method of claim wherein the step 1 image is acquired at a plurality of time points during generation step 1.

5. The computerized image guided step readiness control method of claim 1, wherein the image guided decision performs step characterization to generate at least one step measurement and makes a step status decision using the at least one step measurement to obtain a step decision output.

6. The computerized image guided step readiness control method of claim 5, wherein the step characterization performs characterization entity detection to generate a characterization entity and performs pattern feature extraction from the characterization entity to generate the at least one step measurement.

7. The computerized image guided step readiness control method of claim 5, wherein the step status decision includes a step status decision learning phase and a step status decision application phase.

8. The computerized image guided step readiness control method of claim 7, wherein the step status decision learning phase includes a feature learning step and a decision learning step.

9. The computerized image guided step readiness control method of claim 7, wherein the step status decision application phase includes a feature extraction step and a decision rule application step.

10. A computerized image guided step recovery control method for cell generation having a plurality of generation steps, said method comprising the steps of:
    a) providing at least one source cell and a factor 1 into a cell culture for a cell generation process;
    b) performing generation step 1 in the cell culture by inducing the factor 1 to the at least one source cell obtain a step 1 output;
    c) acquiring a step 1 image into a computer from the step 1 output and performing a computerized image guided decision for the generation step 1 by performing computer image analysis of the step 1 image on the computer to obtain a computerized step 1 decision output;
    d) if the computerized step 1 decision output is "No-Go Recovery", performing recovery process for generation step 1 in the cell generation system: then repeating step c)if a maximum number of allowable decision attempts is not reached, or exiting cell generation if the maximum number of allowable decision attempts is reached;

e) if the computerized step 1 decision output is "No-Go Wait", waiting for a waiting period; then repeating step c) if a maximum number of allowable decision attempts is not reached, or exiting cell generation if the maximum number of allowable decision attempts is reached; and f) if the computerized step 1 decision output is "Go", performing a next generation step in the cell culture by inducing a next factor to the step 1 output to obtain a next step output.

11. The computerized image guided step recovery control method of claim 10, further comprising the steps of:

g) acquiring a next step image from the next step output and performing a computerized image guided decision for the next generation step by performing computer image analysis of the next step image to obtain a computerized next step decision output;

h) if the computerized next step decision output is "No-Go Recovery", performing recovery process for the next generation step; then repeating step g) if a maximum number of allowable decision attempts is not reached, or exiting cell generation if the maximum number of allowable decision attempts is reached;

i) if the computerized next step decision output is "No-Go.Wait", waiting for a waiting period; then repeating step g) if a maximum number of allowable decision attempts is not reached, or exiting cell generation if the maximum number of allowable decision attempts is reached;

j) performing an additional generation step by inducing an additional factor to the next step output if the computerized next step decision output is "Go" and the next generation step is not a final generation step; and k) completing cell generation to obtain target cell if the next generation step is the final generation step.

12. The computerized image guided step recovery control method of claim 10, wherein the method further acquires a source cell image and the image guided decision uses the step 1 image and the source cell image.

13. The computerized image guided step recovery control method of claim 10, wherein the step 1 image is acquired at a plurality of time points during generation step 1.

14. The computerized image guided step recovery control method of claim 10, wherein the recovery process induces at least a factor to promote desired outcome.

15. The computerized image guided step recovery control method of claim 10, wherein the recovery process induces at least a factor to suppress undesired outcome.

16. The computerized image guided step recovery control method of claim 10, wherein the image guided decision performs step characterization to generate at least one step measurement and makes a step status decision using the at least one step measurement to obtain a step decision output.

17. The computerized image guided step recovery control method of claim 16, wherein the step characterization performs characterization entity detection to generate a characterization entity and performs pattern feature extraction from the characterization entity to generate the at least one step measurement.

18. The computerized image guided step recovery control method of claim 16, wherein the step status decision includes a step status decision learning phase and a step status decision application phase.

19. The computerized image guided step recovery control method of claim 18, wherein the step status decision learning phase includes a feature learning step and a decision learning step.

20. The computerized image guided step recovery control method of claim 18, wherein the step status decision application phase includes a feature extraction step and a decision rule application step.

21. A computerized image guided step rejection control method for cell generation having a plurality of generation steps, said method comprising the steps of:

a) providing at least one source cell and a factor 1 into a cell culture for a cell generation process:

b) performing generation step 1 in the cell culture by inducing the factor 1 to the at least one source cell to obtain a step 1 output;

c) acquiring a step 1 image into a computer from the step 1 output and performing a computerized image guided decision for the generation step 1 by performing computer image analysis of the step 1 image on the computer to obtain a computerized step 1 decision output;

d) exiting cell generation if the computerized step 1 decision output is "No-Go Rejection";

e) if the computerized step 1 decision output is "No-Go Wait", waiting for a waiting period; then repeating step c) if a maximum number of allowable decision attempts is not reached, or exiting cell generation if the maximum number of allowable decision attempts is reached; and f) if the computerized step 1 decision output is "Go", performing a next generation step by inducing a next factor to the step 1 output in the cell culture to obtain a next step output.

22. The computerized image guided step rejection control method of claim 21, further comprising the steps of:

g) acquiring a next step image from the next step output and performing a computerized image guided decision for the next generation step by performing computer image analysis of the next step image to obtain a computerized next step decision output;

h) exiting cell generation if the computerized next step decision output is "No-Go Rejection";

i) if the computerized next step decision output is "No-Go Wait", waiting for a waiting period; then repeating step g) if a maximum number of allowable decision attempts is not reached, or exiting cell generation if the maximum number of allowable decision attempts is reached;

j) performing an additional generation step by inducing an additional factor to the next step output if the computerized next step decision output is "Go" and the next generation step is not a final generation step; and k) completing cell generation to obtain target cell if the next generation step is the final generation step.

23. The computerized image guided step rejection control method of claim 21, wherein the method further acquires a source cell image and the image guided decision uses the step 1 image and the source cell image.

24. The computerized image guided step rejection control method of claim 21, wherein the step 1 image is acquired at a plurality of time points during generation step 1.

25. The computerized image guided step rejection control method of claim 21, wherein the image guided decision performs step characterization to generate at least one step measurement and makes a step status decision using the at least one step measurement to obtain a step decision output.

26. The computerized image guided step rejection control method of claim 25, wherein the step characterization performs characterization entity detection to generate a characterization entity and performs pattern feature extraction from the characterization entity to obtain the at least one step measurement.

27. The computerized image guided step rejection control method of claim 25, wherein the step status decision includes a step status decision learning phase and a step status decision application phase.

28. The computerized image guided step rejection control method of claim 27, wherein the step status decision learning phase includes a feature learning step and a decision learning step.

29. The computerized image guided step rejection control method of claim 27, wherein the step status decision application phase includes a feature extraction step and a decision rule application step.

* * * * *